United States Patent
Kneer

(10) Patent No.: US 8,690,013 B2
(45) Date of Patent: Apr. 8, 2014

(54) SINGLE-USE APPLICATOR

(75) Inventor: Roland Kneer, Farchant (DE)

(73) Assignee: Gaplast GmbH, Altenau (DE)

( * ) Notice: Subject to any disclaimer, the term of this patent is extended or adjusted under 35 U.S.C. 154(b) by 139 days.

(21) Appl. No.: 13/192,734

(22) Filed: Jul. 28, 2011

(65) Prior Publication Data

US 2012/0024905 A1    Feb. 2, 2012

(30) Foreign Application Priority Data

Jul. 31, 2010  (DE) .......................... 10 2010 033 015

(51) Int. Cl.
| | | |
|---|---|---|
| *B65D 35/00* | (2006.01) | |
| *B65D 37/00* | (2006.01) | |
| *B65D 47/10* | (2006.01) | |
| *B65D 83/04* | (2006.01) | |
| *B65D 85/42* | (2006.01) | |
| *A61M 35/00* | (2006.01) | |

(52) U.S. Cl.
USPC .......... 222/92; 222/107; 222/541.9; 206/530; 604/310

(58) Field of Classification Search
CPC .... B65D 1/095; B65D 75/5811; B65D 75/32; B65D 75/5822; B65D 1/32; B65D 2221/00; A61M 31/00; A61J 1/067; A45D 40/0087
USPC ................. 222/92, 107, 206, 209, 215, 222/541.1–541.9; 206/528, 530, 531; 215/46–50; 604/2–3, 289, 294–295, 604/310, 415
See application file for complete search history.

(56) References Cited

U.S. PATENT DOCUMENTS

| | | | | |
|---|---|---|---|---|
| 2,103,389 | A * | 12/1937 | Salfisberg ..................... | 222/107 |
| 2,552,100 | A * | 5/1951 | Leonetti et al. ............... | 604/192 |
| 2,744,528 | A * | 5/1956 | Barrett ......................... | 604/212 |
| 3,114,369 | A * | 12/1963 | Hall Victor C ............... | 604/192 |
| 3,207,420 | A * | 9/1965 | Navarrete-Kindelan ....... | 383/38 |
| 4,072,249 | A * | 2/1978 | Ekenstam et al. ............. | 222/95 |
| 4,335,815 | A * | 6/1982 | Babiol et al. ................. | 206/277 |
| 4,512,475 | A * | 4/1985 | Federighi ..................... | 206/484 |
| 4,657,159 | A * | 4/1987 | Grant ............................ | 222/83 |
| 5,215,221 | A * | 6/1993 | Dirksing ....................... | 222/94 |
| 5,425,480 | A * | 6/1995 | Rabenau et al. ......... | 222/153.07 |
| 5,660,273 | A * | 8/1997 | Discko, Jr. .................... | 206/229 |
| 5,996,845 | A * | 12/1999 | Chan ............................. | 222/107 |
| 6,357,627 | B1 * | 3/2002 | Pasbrig et al. ................ | 222/81 |
| 6,460,781 | B1 * | 10/2002 | Garcia et al. ................. | 239/327 |

(Continued)

FOREIGN PATENT DOCUMENTS

| | | |
|---|---|---|
| DE | 69110112 T2 | 11/1995 |
| DE | 19962436 A1 | 7/2001 |
| DE | 10056212 A1 | 5/2002 |
| WO | WO 9622919 A1 * | 8/1996 |

*Primary Examiner* — Paul R Durand
*Assistant Examiner* — Matthew Lembo
(74) *Attorney, Agent, or Firm* — Greer, Burns & Crain, Ltd.

(57) ABSTRACT

The single-use applicator used for discharging a filling substance and comprising a substance receiving chamber provided with an outlet is characterized in that the receiving chamber comprises an outwardly curved wall and an opposite wall which is provided with a surrounding web which engages into the cavity of the curved wall on the edge thereof, and that the curved wall is shaped such that it can be smoothly pressed onto the web and the interposed area of the opposite wall.

13 Claims, 3 Drawing Sheets

(56) References Cited

U.S. PATENT DOCUMENTS

| | | | |
|---|---|---|---|
| 6,666,359 B2* | 12/2003 | Lau et al. | 222/541.5 |
| 6,845,883 B2* | 1/2005 | Pieri | 222/94 |
| 7,097,075 B2* | 8/2006 | Peuker et al. | 222/94 |
| 7,591,398 B2* | 9/2009 | Pritikin et al. | 222/80 |
| 7,625,114 B2* | 12/2009 | Suchan et al. | 366/130 |
| 7,717,281 B2* | 5/2010 | Baudin | 215/235 |
| 7,922,021 B2* | 4/2011 | Golden | 220/4.22 |
| 7,971,739 B2* | 7/2011 | Ammann | 215/257 |
| 8,141,709 B2* | 3/2012 | Klaus | 206/484 |
| 2002/0104856 A1* | 8/2002 | Clark et al. | 222/633 |
| 2007/0228073 A1* | 10/2007 | Mazzarino | 222/107 |
| 2008/0123465 A1* | 5/2008 | Heusser et al. | 366/130 |
| 2008/0289989 A1* | 11/2008 | Kalvelage et al. | 206/531 |
| 2009/0071978 A1* | 3/2009 | Sharp et al. | 222/107 |

* cited by examiner

Section A-A

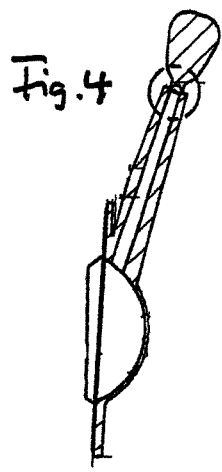
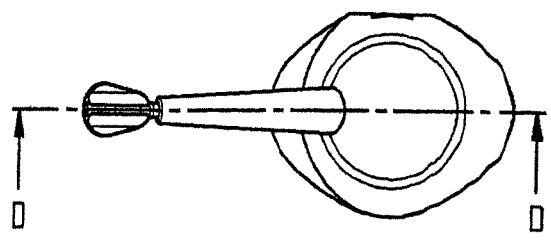
Section B-B
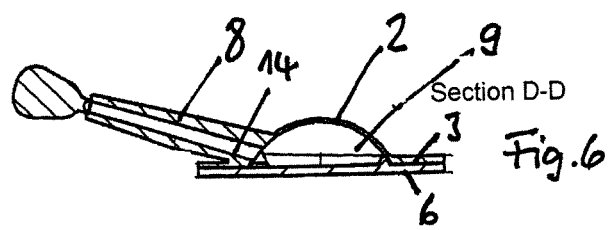
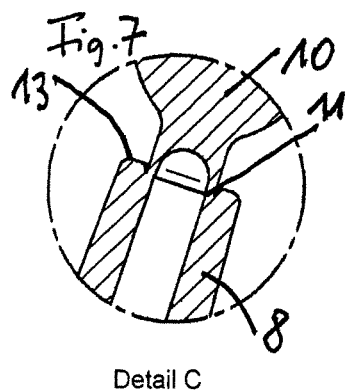
Detail C

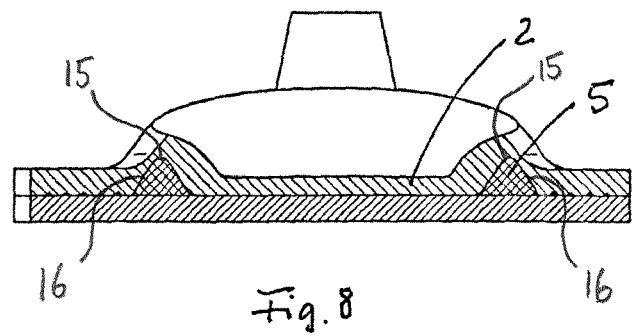

SINGLE-USE APPLICATOR

FIELD OF THE INVENTION

The present invention refers to a single-use applicator for discharging a filling substance, the applicator comprising a substance receiving chamber provided with an outlet.

SUMMARY

The single-use applicator is particularly configured to discharge the whole filling substance in one single operation. However, it is also within the scope of the present invention that the container contents can be discharged in two or more partial doses. The filling substance is preferably a viscous or creamy container contents, but the single-use applicator is also suited for discharging a substance of low viscosity.

The container contents can e.g. be a pharmaceutical substance which is introduced into a user's nose without the invention being limited thereto.

Such single-use applicators, which may have a small volume in the order of a cubic centimeter or less, have, in general, the shape of a small bottle and for the discharge of the container contents they are squeezed at the side so as to press out the container contents. So far quite a considerable residual amount has remained in the compressed container and could not be discharged.

It is the object of the present invention to indicate a single-use applicator in which virtually the whole container contents can be discharged, except for a negligible residual amount.

Said object is achieved according to the invention by a single-use applicator for discharging a filling substance, comprising a substance receiving chamber provided with an outlet, characterized in that the receiving chamber comprises an outwardly curved wall and an opposite wall which is provided with a surrounding web which engages into the cavity of the curved wall on the edge thereof, and that the curved wall is shaped such that it can be smoothly pressed onto the web and the interposed area of the opposite wall.

Advantageous developments of the invention are characterized below.

According to the invention the single-use applicator comprises a receiving chamber for the filling substance, the chamber consisting of an outwardly curved wall and an opposite wall, the latter being provided with a surrounding web which engages into the cavity of the curved wall on the edge thereof, and that the curved wall is shaped and dimensioned such that it can be smoothly pressed onto the web and the interposed area of the opposite wall. In the compressed state the curved wall rests substantially without any remaining clearance on the web and the opposite wall so that virtually the whole contents is pressed out of the receiving chamber without a significant residual amount being left since the curved wall smoothly abuts around the web on the opposite wall without the formation of folds. The web which preferably has a substantially conical shape in cross-section, with rounded-off tip and slightly rounded flanks, thereby fills the space that is automatically formed when a curved wall is squeezed on its outer edge. Since this space is filled by the web, no residual amount of the container contents can remain there.

The curved wall preferably has the shape of a spherical cap, the web then projecting circularly from the opposite wall.

The curved wall, however, may also have an oval layout, the surrounding web then having a corresponding oval shape in its layout.

The opposite wall which defines the receiving chamber is preferably planar. However, it is also within the scope of the invention that said wall may also be curved preferably outwardly, said curvature then having a flatter extension, so that the other wall can be smoothly pressed on.

Furthermore, according to the invention the outwardly curved wall and the opposite wall have each a planar surrounding edge, and said edges are fastened to each other.

Preferably, it is here provided that said edge portions are welded to each other, preferably by ultrasonic welding, and that they are provided with small grooves on their surfaces facing each other in the initial state—prior to welding.

According to a further proposal of the invention the outlet of the single-use applicator by which the filling substance is discharged is formed by a small tube that is mounted on the curved wall and opens towards the receiving chamber.

The free end of the small tube is preferably closed by a tear-off plug or pin which is inwardly mounted on the small tube with a thin tear-off seam. For discharging the container contents the pin is removed from the small tube e.g. by being turned about its longitudinal axis. Since the tear-off seam is positioned in the interior of the small tube, no remaining ridge will project from the small tube during use, so that the small tube cannot cause any injury if it is e.g. introduced into a user's nose.

It is further suggested with great advantage that the single-use applicator is integrally formed by injection molding, the edges of the two walls of the receiving chamber being connected with a film hinge. First of all the cavity of the curved wall is here filled with container contents, whereupon the opposite wall is folded over on the film hinge and is placed with its edge on the edge of the curved wall, with the surrounding web ensuring the centering of the two housing halves. Subsequently, the edges are welded. Especially when the opposite wall is planar, the whole receiving chamber can thereby be filled completely.

For instance, polyolefins such as PP or PE are suited as materials for the single-use applicator without the invention being limited thereto.

The curved wall expediently has a smaller wall thickness than the opposite wall and the edges, so that the receiving chamber can be pressed together without any problems. For instance, the wall thickness of the curved wall is 0.2 mm to 0.3 mm while the opposite, preferably planar wall and the two edges may have a thickness of 0.6 mm, whereby they have the stability needed for welding.

In the single-use applicator according to the invention, virtually the whole container contents can be pressed out, which is particularly desirable in the case of a viscous or creamy filling substance that cannot flow out from the applicator by way of gravity. A further great advantage of the applicator according to the invention is that it can be integrally produced by injection molding at low costs.

Further details of the invention become apparent from the following description and with the help of the drawings, in which

BRIEF DESCRIPTION OF THE DRAWINGS

FIG. 4 is a section B-B in FIG. 2;

FIG. 5 is a top view on the assembled single-use applicator;

FIG. 6 is a section D-D in FIG. 5;

FIG. 7 shows a detail C in FIG. 4, and

FIG. 8 is a longitudinal section through the single-use applicator in the squeezed-out state.

DETAILED DESCRIPTION OF PREFERRED EMBODIMENTS

Figure 1:
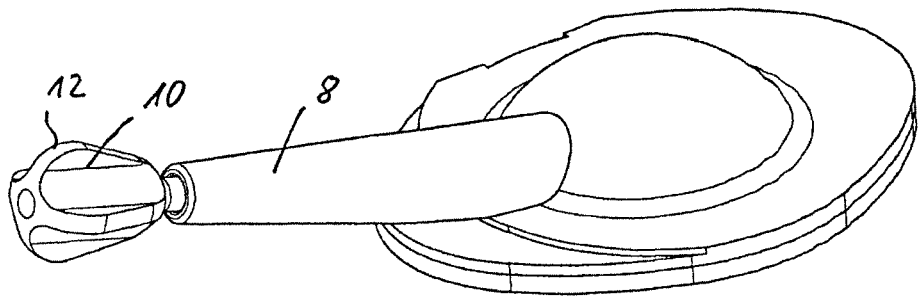
FIG. 1 is a perspective view of the finished single-use applicator on an enlarged scale.
Figure 2:
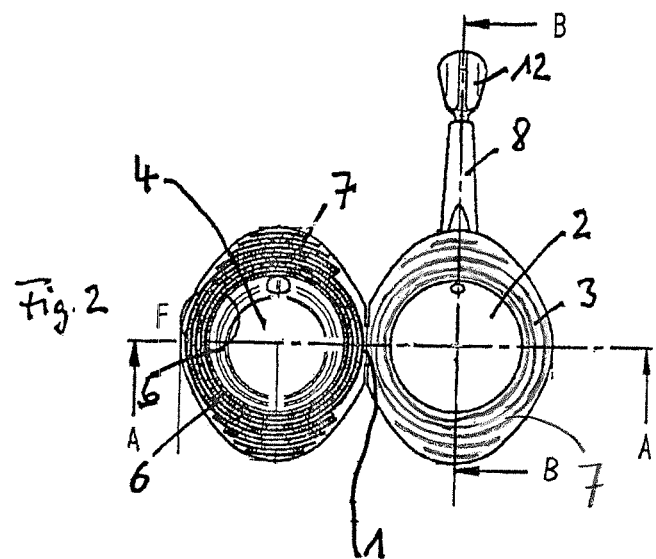
FIG. 2 is a top view on the blank of the single-use applicator in the opened initial state.
Figure 3:
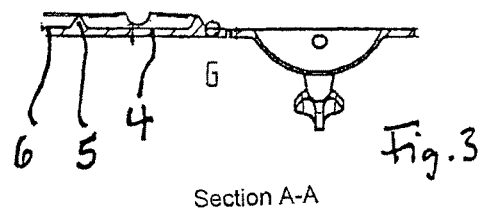
FIG. 3 is a section A-A in FIG. 2.

FIG. 2 shows the single-use applicator in the state in which it leaves the injection mold. The single-use applicator is composed of two container halves that are interconnected by a film hinge 1. The right container half in FIG. 2 includes a curved wall 2 which has the shape of a spherical cap surrounded by a planar edge 3.

The other container half consists of a planar wall 4 from which a web 5 of an approximately conical cross-section and shaped as a circular ring is protruding, which web is followed on the outside by an also planar edge 6. The outer contours of the edges 3 and 6 are identical. The edges 3 and 6 are provided with grooves 7.

A small tube 8 which is open towards the receiving chamber 9 of the single-use applicator is formed on the curved wall 2. Prior to discharge of the container contents the small tube 8 is closed by a tear-off pin 10 which is mounted with a thin tear-off seam 11 in the interior of the small tube 8 (FIG. 7). The tear-off pin 10 has a profiled head 12 with which the tear-off pin 10 can be easily twisted off from the small tube 8. The tear-off seam is receded from the face 13 of the small tube 8, so that no ridge will protrude from the face 13.

The web 5 which is shaped as a circular ring has a small recess in the area of the channel 14 of the small tube 8, so that the web 5 does not obstruct the exit of the container contents through the small tube 8. The web 5 which preferably has a substantially conical shape in cross-section, with rounded-off tip 15 and slightly rounded flanks 16, thereby fills the space that is automatically formed when a curved wall 2 is squeezed on its outer edge. Since this space is filled by the web 5, no residual amount of the container contents can remain there.

FIG. 8 shows the squeezed-out state of the single-use applicator. When a curved wall is pressed inwards in opposition to its curvature, an annular cavity that would not be completely compressible by a user's finger is automatically formed on the outer edge thereof. Without the web in the form of a circular ring 5 container contents would here automatically remain and could not be discharged. In the single-use applicator according to the invention this edge portion is filled by the web 5, which substantially has a conical cross-sectional shape, so that virtually the whole container contents can be discharged.

The invention claimed is:

1. A single-use applicator for discharging a filling substance, comprising
an outwardly curved wall and an opposite wall forming a substance receiving chamber,
wherein the substance receiving chamber has an outlet, and the opposite wall includes a surrounding web,
wherein the web has a substantially arched cross-section with a rounded-off tip and substantially rounded flanks, wherein the web occupies the substance receiving chamber and substantially surrounds an edge of the substance receiving chamber formed by the outwardly curved wall and the opposite wall,
wherein the curved wall is sized, shaped, and configured to be depressed, thereby reducing a volume of the substance receiving chamber, wherein the curved wall conforms to and presses against the opposite wall and the web to dispense substantially all of contents from the substance receiving chamber, and
wherein the curved wall has the shape of a spherical cap and the single-use applicator is integrally formed by injection molding, the edges of the two walls being connected by a film hinge.

2. A single-use applicator according to claim 1, wherein the curved wall has an oval layout.

3. A single-use applicator according to claim 1, wherein the opposite wall is planar.

4. A single-use applicator according to claim 1, wherein the opposite wall is also curved.

5. A single-use applicator according to claim 1, wherein the outwardly curved wall and the opposite wall have each a planar surrounding edge and that said edges are fastened to each other.

6. A single-use applicator according to claim 5, wherein the edges are welded to each other.

7. A single-use applicator according to claim 5, wherein each of the edges has a plurality of grooves.

8. A single-use applicator according to claim 1, wherein the outlet is formed by a small tube which is formed on the curved wall and opens towards the receiving chamber.

9. A single-use applicator according to claim 8, wherein the free end of the small tube is closed by a tear-off pin which is inwardly mounted on the small tube.

10. A single-use applicator according to claim 1, wherein the curved wall has a smaller wall thickness than the opposite wall and the edges.

11. A single-use applicator according to claim 1, wherein the surrounding web is detached from the outwardly curved wall.

12. A single-use applicator for discharging a filling substance, comprising
an outwardly curved wall and an opposite wall forming a substance receiving chamber,
wherein the substance receiving chamber has an outlet,
wherein the opposite wall includes a surrounding web having a substantially arched cross-section with a rounded-off tip and substantially rounded flanks, wherein the web is shaped as a ring substantially surrounding the substance receiving chamber,
wherein the curved wall is sized, shaped, and configured to be depressed, thereby reducing a volume of the substance receiving chamber, wherein the curved wall conforms to and presses against the opposite wall and the web to dispense substantially all of contents from the substance receiving chamber, and
wherein the curved wall has the shape of a spherical cap, and the curved wall has a smaller wall thickness than the opposite wall.

13. A single-use applicator for discharging a filling substance, comprising
an outwardly curved wall and an opposite wall forming a substance receiving chamber,
wherein the substance receiving chamber has an outlet, and the opposite wall includes a surrounding web,
wherein the web has a substantially arched cross-section with a rounded-off tip and substantially rounded flanks, wherein the web occupies the substance receiving chamber and substantially surrounds an edge of the substance receiving chamber formed by the outwardly curved wall and the opposite wall,
wherein the curved wall is sized, shaped, and configured to be depressed, thereby reducing a volume of the substance receiving chamber, wherein the curved wall conforms to and presses against the opposite wall and the web to dispense substantially all of contents from the substance receiving chamber, and wherein the opposite wall is planar, and the outwardly curved wall and the opposite wall have each a planar surrounding edge and that said edges are fastened to each other.

\* \* \* \* \*